United States Patent [19]

Franetzki et al.

[11] Patent Number: 4,776,842
[45] Date of Patent: Oct. 11, 1988

[54] DEVICE FOR THE ADMINISTRATION OF MEDICATIONS

[75] Inventors: Manfred Franetzki, Uttenreuth; Karl Prestele, Erlangen, both of Fed. Rep. of Germany

[73] Assignee: Siemens Aktiengesellschaft, Berlin and Munich, Fed. Rep. of Germany

[21] Appl. No.: 846,765

[22] Filed: Apr. 1, 1986

Related U.S. Application Data

[63] Continuation-in-part of Ser. No. 543,182, Oct. 18, 1983, abandoned.

[51] Int. Cl.⁴ .............................................. A61M 5/00
[52] U.S. Cl. ............................... 604/67; 128/DIG. 13
[58] Field of Search ................................... 604/65–68, 604/151, 131, 246; 128/DIG. 12, DIG. 13; 222/59

[56] References Cited

U.S. PATENT DOCUMENTS

| | | | |
|---|---|---|---|
| 2,979,055 | 4/1961 | de Beer et al. | 128/214 |
| 4,275,727 | 6/1981 | Keeri-Szanto | 128/DIG. 13 |
| 4,395,259 | 7/1983 | Prestele et al. | 604/67 |
| 4,469,481 | 9/1984 | Kobayashi | 604/67 |
| 4,475,901 | 10/1984 | Kraegen et al. | 604/66 |

FOREIGN PATENT DOCUMENTS 0019814 12/1980 European Pat. Off. .
0038080 10/1987 European Pat. Off. .

Primary Examiner—Stephen C. Pellegrino
Attorney, Agent, or Firm—Mark H. Jay

[57] ABSTRACT

The invention relates to an apparatus for the administration of medications. The apparatus includes a safety system which prevents a harmful overdose when the person using the apparatus is unable to take action. For this purpose, the safety system initiates a safety measure, (such as turning off the dosing unit, switching the dosing unit to a reduced administration rate (so called "emergency rate") and/or setting off an alarm) in the event that a checking procedure is not triggered by the patient within a predetermined time interval or after the administration of a specific quantity of medication. Starting times based on the time of day and generated by a master clock can be pre-pregrammed, for example, as a reminder to the patient to eat. In insulin therapy, the apparatus prevents a patient from becoming hypoglycemic as the result of a long lasting insulin overdose, for example, during sleep.

11 Claims, 5 Drawing Sheets

DEVICE FOR THE ADMINISTRATION OF MEDICATIONS

CROSS REFERENCE TO RELATED APPLICATION

This application is a continuation-in-part of commonly-owned application Ser. No. 543,182 filed Oct. 18, 1983 now abandoned.

BACKGROUND OF THE INVENTION

The invention is related to a device or an apparatus for the administration of medication, and it includes a controllable dosing unit and a control or programming unit. If so desired, the programming unit may be located or positioned separately from the dosing unit.

Apparatuses or devices of this type are designed for the continuous infusion of liquid medications, such as heparin, cytostatics, analgesics, insulin and other hormones. The infusion rate can be programmed in advance; it may be constant or may vary in a cyclical manner (for example according to a daily profile) over a considerable time period. Alternatively, the infusion rate can be adjusted by hand using suitable operating elements. The infusion rate can also be adjusted to the current requirements dictated by the patient's need as detected by a sensor. When such an apparatus is used at bedside or worn on the body, a catheter is introduced from the device into the body. The apparatus can also be implanted, in which case an external control or programming unit is generally used to control and/or program the infusion rate. Apparatuses of this kind are currently available from various manufacturers, and are described in medical literature.

Continuous, controlled or programmed infusion has the advantage, in comparison with conventional forms of therapy (such as oral administration of medication or injections) that the dosage of the medication is more accurate and can be better adapted to the actual medication need or requirements, which may be constant or may fluctuate.

Under certain circumstances, however, such infusion entails a disadvantage as compared to conventional forms of therapy, because the introduction of medications into the body is not automatically limited to a specified dose. This can lead to an overdose which can be dangerous for the patient under certain circumstances, particularly when loss of consciousness, loss of sleep or even failure to pay attention prevents the patient from reducing or turning off the infusion when the infusion rate has been set too high. This will now be discussed with specific exemplary reference to diabetes therapy using insulin.

Devices for programmed or controlled dosing of medications are used for example, in diabetes therapy for continuous insulin infusion. The infusion rate can either be programmed in advance for a long time period (for example, with a cyclically repeating 24-hour program), or can be adjusted by the patient to his current needs, with the aid of suitable operating elements. For example, the infusion rate can be set to a fundamental basal rate that is either constant over time or programmed according to a daily profile; there can then be added at each meal a supplementary rate of limited duration. This supplementary rate takes into account the higher need for insulin during the digestion of carbohydrates.

If the insulin requirement has been incorrectly estimated or if it changes unexpectedly, due, for example, to illness, mental excitement or unaccustomed bodily activity, the result may be an overdose of insulin, causing under certain circumstances a hypoglycemic condition associated with illness and even loss of consciousness. Hypoglycemic conditions of this kind are particularly dangerous when they occur during sleep, because it is then impossible to take compensatory measures (e.g. reducing or turning off completely the insulin infusion or administering glucose) promptly, and it may be impossible to take them at all. In the most serious cases, irreversible brain damage or even death of the patient can result. Whereas in conventional injections the insulin dose injected into the body is limited by the volume of the syringe and used up after a certain time, in continuous infusions the application of insulin is continued even when the patient is unconscious or otherwise incapable of acting. This is a disadvantage of automatic dosing devices as a class, and can also occur in similar manner in connection with the infusion of medications other than insulin that have critical dosages.

SUMMARY OF THE INVENTION

An object of this invention is to provide an apparatus for the administration of medication which can automatically initiate a safety measure if the patient is unable to operate the apparatus.

Another object of this invention is to provide an apparatus for the automatic administration of insulin that is safe in operation and protects the patient.

According to the invention, the apparatus includes means for initiating a safety measure (such as turning off the dosing device or switching it to a reduced administration rate—the so-called "emergency rate"—and/or setting off an alarm) if the patient fails to initiate a checking procedure in accordance with a predetermined criterion, i.e. within a specific interval of time, or prior to the administration of a predetermined volume of medication. In the following the term "reduced administration rate" means a smaller administration rate, and includes a zero rate. Reduction to a zero rate will usually require turning the dosing unit off.

The invention prevents a long lasting overdose when an automatic device for the administration of medications is used. The advantage of automatic dosing of medications in comparison with the conventional forms of administration, which were described earlier, is fully preserved.

The invention can be realized in practice in three preferred embodiments:

(a) After the execution of a checking procedure performed by the patient, the infusion according to the program is permitted to continue for a limited time. This time may be either rigidly prescribed or adjustable, and is hereinafter referred to as the "qualifying time", If no further checking procedure is executed during the qualifying time, the safety measure(s) is automatically activated.

(b) After the execution of a checking procedure performed by the patient, the infusion according to the program is permitted to deliver a limited maximum dose. This does may be either rigidly prescribed or adjustable, and is hereinafter referred to as the "qualifying dose". If no further checking procedure is executed before a qualifying does of medication is delivered, the safety measure (a) is automatically activated.

(c) Waiting intervals, based on time of day, hereinafter referred to as "qualifying intervals", are prescribed and adjusted to the daily living rhythm or the daily requirements of the patient. If the patient executes the checking procedure within a first qualifying interval, the infusion according to the program is permitted to continue until the expiration of the next or second qualifying interval. On the other hand, if the patient fails to execute the checking procedure, the safety measure (s) is automatically activated at the end of the first qualifying interval.

The term "adjustable" as used herein, includes a fixed adjustment of the control unit by the manufacturer as well as a user-controlled adjustment of the qualifying time, the qualifying dose or the qualifying interval by himself according to his actual requirements.

The above embodiments (a), (b) and (c) can advantageously be combined in a single unit.

The checking procedure according to the invention can either be identical to or performed simultaneously with a procedure that is normally required for the use of the apparatus. For example, it can be performed along with the activation of the call switch in call-controlled insulin-dosing devices, in which case no additional operating element (such as a switch or pushbutton) is needed. On the other hand, the checking procedure can be implemented by means of an additional operating element (such as a switch or pushbutton), in the case of devices with constant or cyclically pre-programmed infusion rates, which need no regular patient operation in order to, for example, control the infusion rates.

According to another embodiment of the invention, a signalling device can be activated at the beginning of a pre-programmed qualifying interval. This reminds the patient to, for example, eat a meal and to carry out the appropriate checking procedures. This makes it possible to ensure that at the pre-programmed time which represents the beginning of the qualifying interval (for example, at the beginning of breakfast, lunch or dinner) a reminder signal is given to remind the patient to execute the operational and/or checking procedure. In particular in the case of automated, call-controlled insulin administration this procedure can be triggered by the activation of the call switch for the additional dose of insulin or any other switch or button already incorporated in the dosing unit, prior to the beginning of digestion.

If in spite of the reminder signal the qualifying interval elapses without the checking procedure having been performed, the safety mesure again becomes activated to protect the patient. It is desirable that the reminder signals generated at the beginning of the qualifying interval differ from those generated at the end of the qualifying interval. For example, individual or periodic acoustic signals can first be generated as a command for the patient at the beginning of the qualifying interval, while after expiration of the qualifying interval a persisting and more penetrating alarm signal can be given in order to attract the attention of not only the patient, but also of persons around him. In this case the signalling device and the alarm device can form a single unit, with the different signals being distinguished by their noise level, frequency of repetition and/or other characteristics.

Other features and advantages of the present invention will become apparent from the following detailed description and from the claims.

For a full understanding of the present invention, reference should now be made to the following detailed description and to the accompanying drawings.

DETAILED DESCRIPTION OF THE DRAWINGS

Figure 1:
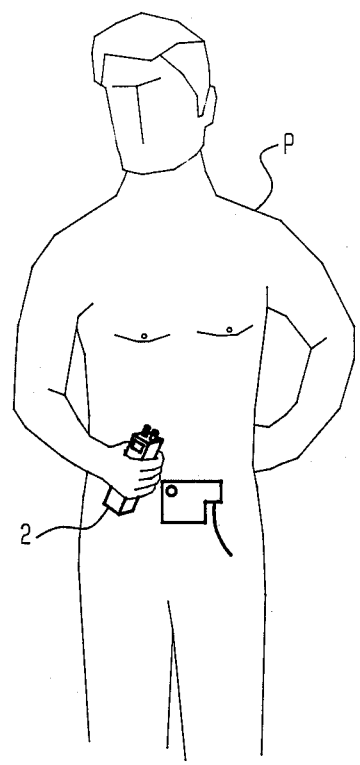
FIG. 1 shows a patient with an implanted, remotely programmable apparatus for the administration of medications.

Throughout the description, the same element is always indicated by the same reference numeral and analogous elements are indicated with primes.

Referring to FIG. 1, a patient P is shown with an abdominally implanted medication-dosing unit 1, and an external programmable unit or control unit 2. Dosing units of this kind are well-known in the art and are described, for example, in published German patent application No. DE-OS 29 20 976. Dosing units of this type can also be used outside the body and connected to the patient's body by means of a catheter. The control unit 2 can then be combined with the dosing unit 1 to form a single functional unit.

Figure 2:
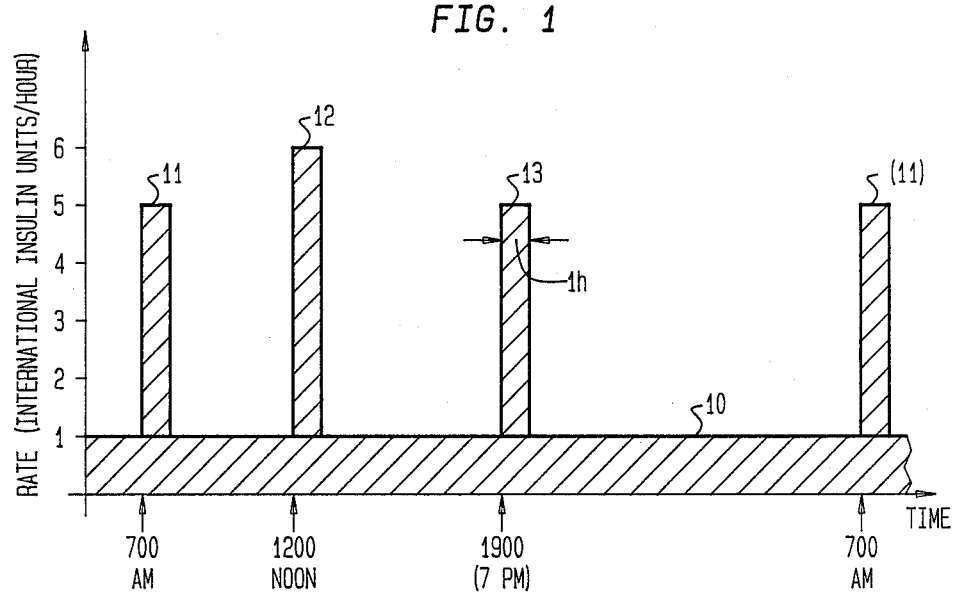
FIG. 2 shows a daily infusion profile for call-controlled insulin dosing.

FIG. 2 shows an example of an infusion profile for a 24 hour period which is typical of the so-called call-controlled insulin dose in diabetes therapy. The time is shown on the X-axis and the infusion rate R is shown on the Y-axis for a period of slightly more than 24 hours. A constant basal infusion rate 10 may amount to for example one international insulin unit per hour (1 IU/h). To the basal rate 10 there can be added at mealtimes supplementary rates 11, 12 and 13, which for instance may be chosen to correspond to the carbohydrate content of the respective meal. The hatched area represents the total infused insulin dose.

In order to add the supplementary rates to the basal rate, the patient must initiate an appropriate procedure, for instance by pushing a call button. This is symbolized in FIG. 2 by the respective arrows along the X axis. In the example shown, these operational procedures take place at 7:00 a.m., 12:00 noon and 7:00 p.m. (19:00 hours). Depending upon the design used, for this example a qualifying time of about 13 hours, a qualifying dose of about 20 insulin units and qualifying intervals from 6 to 8 a.m., from 11 a.m. to 1 p.m. and from 6 to 8 p.m. respectively, would be appropriate.

In the example shown, a more conservative limitation on overdosing would be achieved during the course of the day with the qualifying intervals as presented than with the qualifying time or qualifying dose, because the latter must be chosen to be relatively large due to the long time between dinner and breakfast. A closer limitation of the qualifying dose would be possible if the basal rate above were taken into account for the integration of the qualifying dose. In this case, in the example of FIG. 2 a qualifying dose of approximately 13 insulin units would be suitable.

Figure 3A:
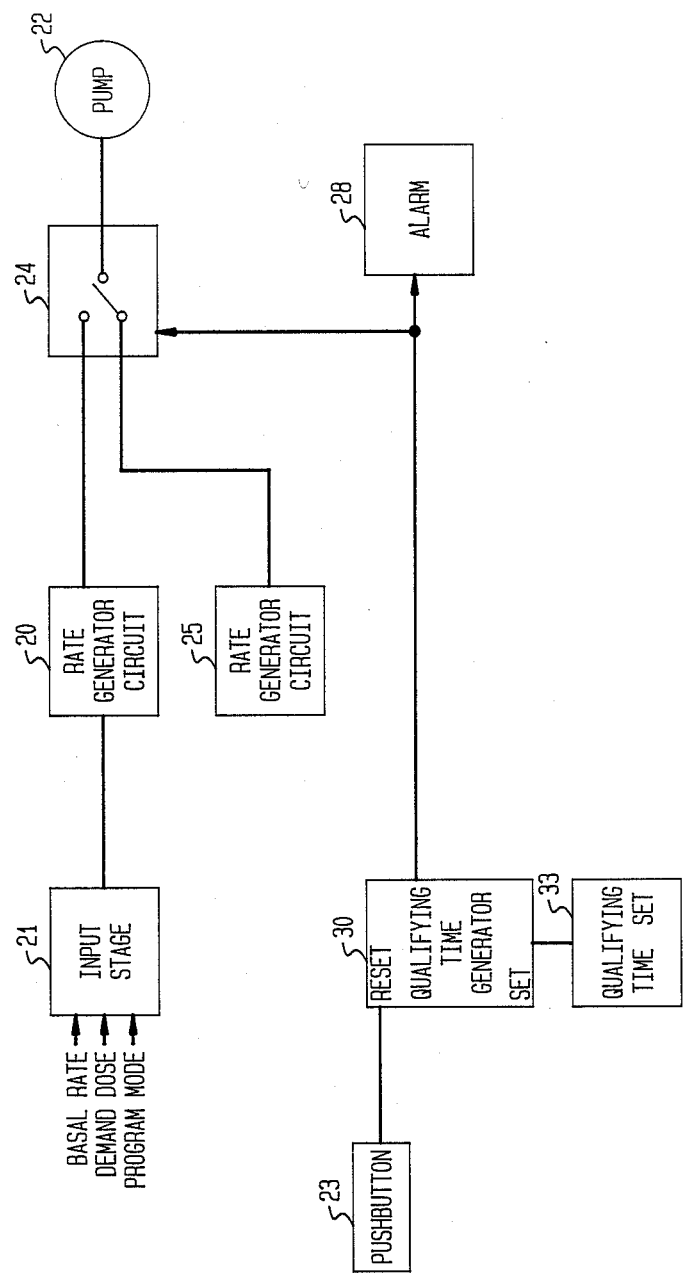
FIG. 3A shows schematically a first embodiment of the invention using a qualifying time generator.

In FIG. 3A, a dosing pump 22 delivers medication from a reservoir (not shown) to the patient (not shown). The pump 22 may be driven by a stepping motor or by a DC motor. An input stage 21 receives information about the dosage profile required for a particular patient and converts this information into a suitable form for controlling a rate generator circuit 20. Where the pump 22 is driven by a stepping motor, the rate generator circuit 20 is a frequency generator; where the pump 22 is driven by a DC motor, the rate generator circuit 20 is a voltage generator. In normal operation, the switch 24 (which may be an electrical or miniaturized mechanical version of a single-pole double-throw switch) connects the pump 22 to the rate generator circuit 20.

A qualifying time generator 30 (such as a combination of a digital clock generator and a digital electronic counter) can be programmed by a qualifying time set unit 33 to produce a logically high output when the qualifying time is reached. A pushbutton 23 is connected to the reset input of the qualifying time generator 30. When the pushbutton 23 is operated by a patient before the qualifying time generator has reached the time programmed into it by the qualifying time set unit 33, the timing process is restarted once again from the beginning. However, if the qualifying time generator 30 is not reset by patient operation of the pushbutton 23, the qualifying time generator 30 produces a logically high output which energizes the alarm 28 and switches the switch 24 so as to disconnect the rate generator circuit 20 from the pump 22 and to connect the rate generator circuit 25 to the pump 22 instead. Where the pump 22 is a stepping motor, the rate generator circuit 25 is a frequency generator; where the pump 22 is a DC motor, the rate generator circuit 25 is a voltage generator.

The rate generator circuit 25 is adjusted so that the pump 22 delivers medication at a reduced emergency rate or even at a zero rate. Thus, when the patient fails to actuate the pushbutton 23 before the passage of the qualifying time, the alarm 28 will be operated to alert the patient and those around him and the pump 22 will be slowed down to deliver medication at a reduced emergency rate (which may be zero).

In this example, the patient is not required to perform any actions to keep the unit operating, so the pushbutton 23 has no function other than to indicate that the patient is alive and capable of acting for himself. However, if the patient is required to carry out any checking procedures (e.g. to test the battery, check for an adequate quantity of insulin, etc.), the pushbutton 23 or other appropriate control may be adapted to perform a dual function.

Figure 3B:
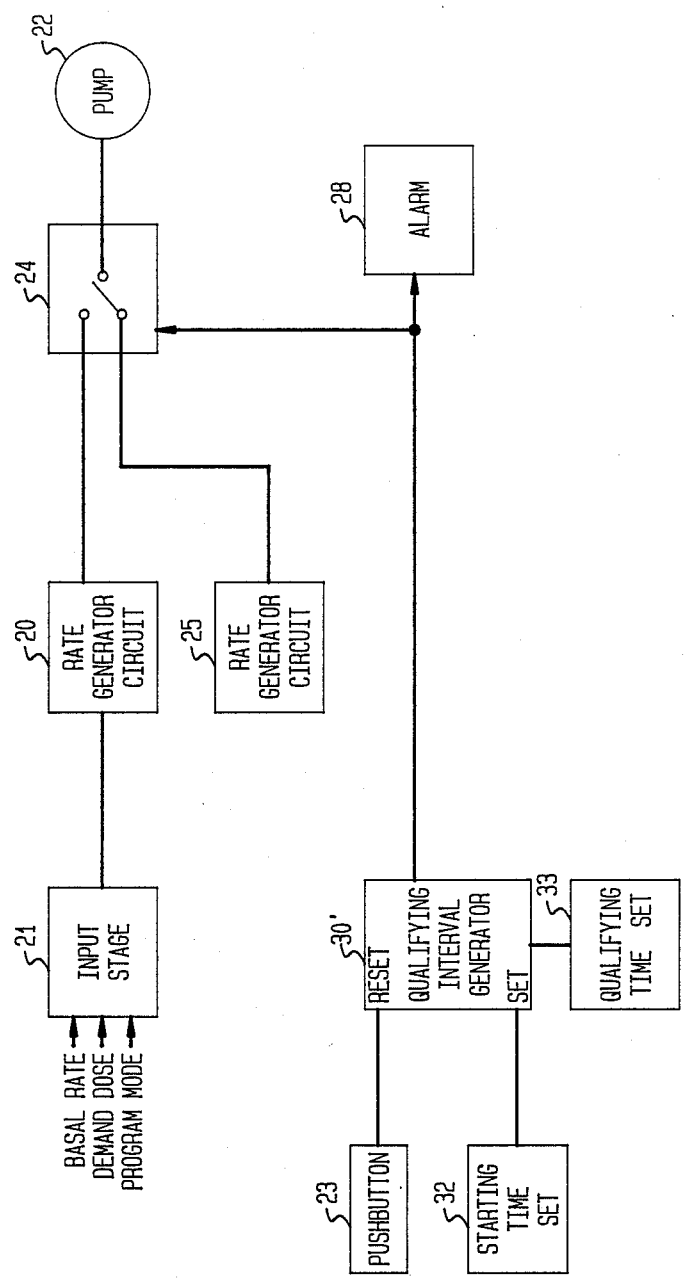
FIG. 3B shows schematically a first embodiment of the invention using a qualifying interval generator.

Referring now to FIG. 3B, it can be seen that the alarm 28 and switch 24 are now operated by a qualifying interval generator 30'. In this example, the qualifying interval generator 30' may be the same combination of clock and counter that was used in the qualifying time generator 30 of FIG. 3A, but reconfigured so that counting does not begin until the set input of the qualifying interval generator 30' receives an input from a starting time set unit 32. In the FIG. 38 embodiment, the starting time set unit 32 (which may itself be a combination clock and counter) sets the qualifying interval generator 30' counting at a desired time. This starts the timing of the qualifying time which is set by the qualifying time set unit 33. If the pushbutton 23 is operated within the qualifying interval, the qualifying interval generator 30' never produces a logically high output and the pump 22 remains controlled by the rate generator circuit 20 in accordance with the information inputted into the input stage 21. However, as in the previous case, where the pushbutton 23 is not actuated within the qualifying interval, the alarm 28 is turned on and the switch 24 is set to disconnect the pump 22 from the rate generator circuit 20 and to connect it to the rate generator circuit 25, which causes the pump 22 to deliver the medication at a reduced emergency rate (which may be zero).

Figure 4:
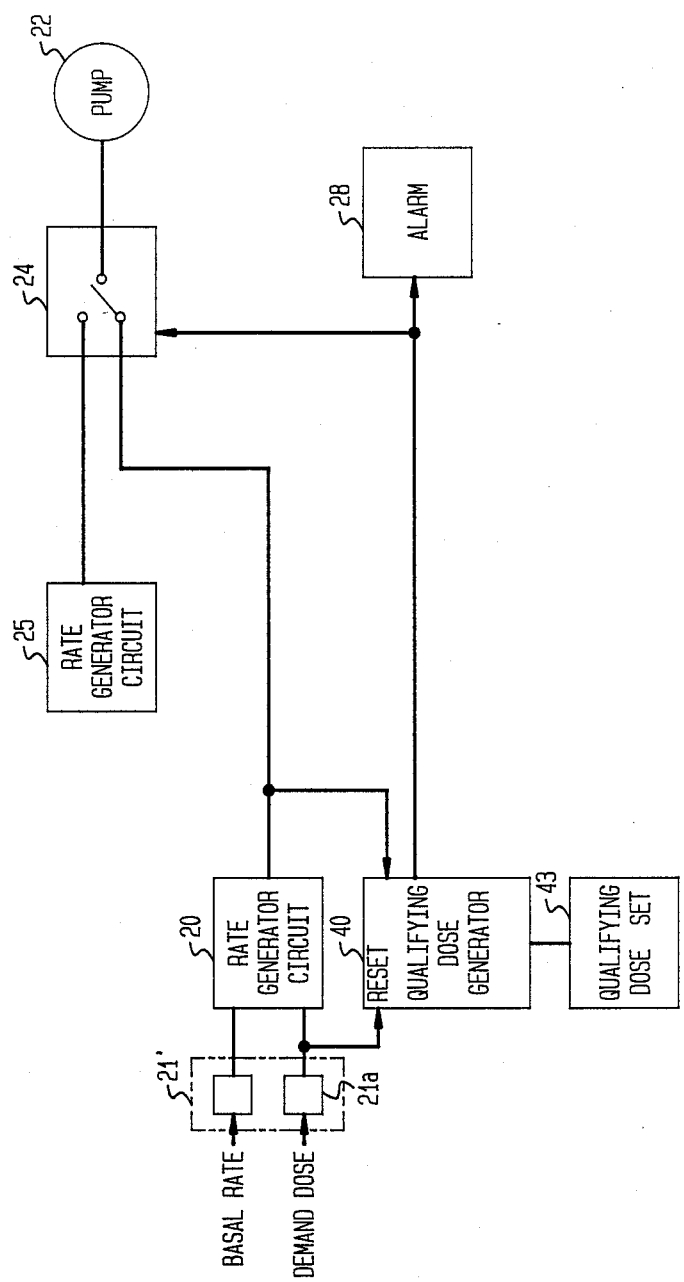
FIG. 4 shows schematically a second embodiment of the invention using a qualifying-dose generator.

In FIG. 4, the input stage 21' is configured so that a patient may cause an additional dose of medication to be administered to himself by operation of a call switch 21a. This is used for example to increase the rate at which medication is delivered to cope with a patient's needs during e.g. mealtimes.

In this example, the circuit previously configured as either a qualifying time generator or a qualifying interval generator is now configured as a qualifying dose generator 40 (as by disabling the clock and responding instead to the output of the rate generator circuit 20). Here, the qualifying dose generator 40 adds up the dose of medication delivered by the pump 22 (as represented by the output from the rate generator circuit 20) and generates a logically high output signal if this dose exceeds a qualifying dose which is determined by the qualifying dose set unit 43. When the patient operates the call switch 21a at e.g. the beginning of a meal, the qualifying dose generator 40 is reset and does not operate either the alarm 28 or the switch 24. However, when the qualifying dose generator 40 determines that the rate generator circuit 20 has caused the total dosage delivered by the pump 22 to the patient to equal or exceed the qualifying dose established by the qualifying dose set unit 43 without activation of the call switch 21a, the alarm 28 is energized and the pump 22 is disconnected from the rate generator circuit 20 and connected to the rate generator circuit 25, for delivering medication at a reduced (perhaps to zero) emergency rate.

Figure 5:
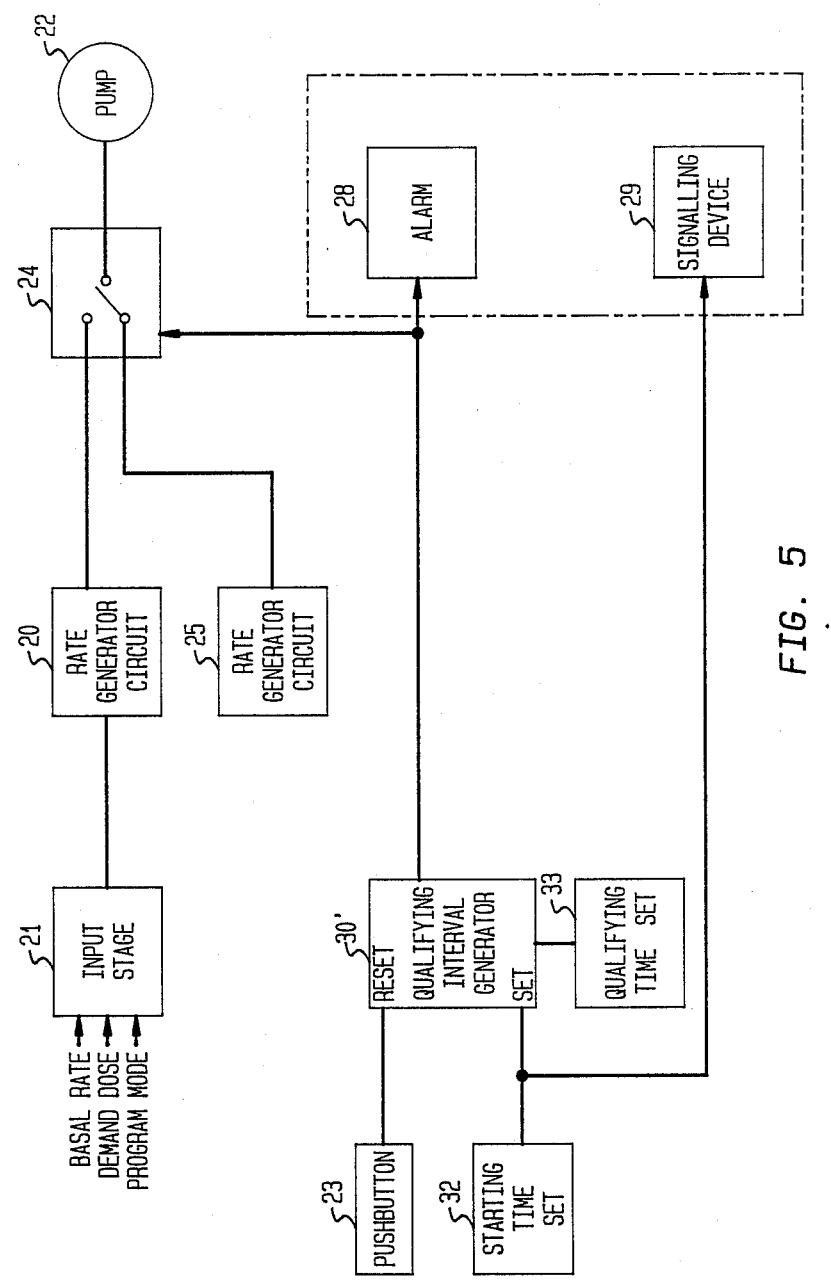
FIG. 5 shows schematically a third embodiment of the invention using a qualifying-interval generator and an alarm device.

In the embodiment of FIG. 5, operation is identical to the embodiment of FIG. 3B, except for the operation of the signalling device 29. In this example, a signalling device 29 is connected to the output of the starting time set unit 32. Thus, at the beginning of the qualifying interval established by a logically high output from the starting time set unit 32, the signalling device 29 is operated to inform the patient that he should begin to eat and should push the pushbutton 23 when he has begun to do so. The sound produced by the signalling device 29 is different from the sound produced by the alarm 28; the signalling device 29 preferably produces a sound which is audible only to the patient, while the sound produced by the alarm 28 is preferably loud enough to alert others. As is schematically illustrated in FIG. 5, the alarm 28 and signalling device 29 may advantageously be combined into a single unit.

The safety measures described above can also be combined with other qualifying time or qualifying dose generators to form a functional unit, for example, such that the safety circuit responds immediately when either the qualifying time has elapsed or the qualifying dose is reached before an expected operating procedure has taken place. This function makes possible a specific adaptation to the conditions that exist in each individual case.

There has thus been shown and described a novel apparatus for the administration of medications which fulfills all the objects and advantages sought. Many changes, modifications, variations and other uses and application of the subject invention will, however, become apparent to those skilled in the art after considering this specification which discloses embodiments thereof. All such changes, modifications, variations and other uses and applications which do not depart from the spirit and scope of the invention are deemed to be covered by the invention which is limited only by the claims which follow.

What is claimed is:

1. A sensorless device for administration of medication, comprising:
   means for establishing a rate at which medication is to be administered, said establishing means being adjustable in a manner that said rate can be varied between an emergency rate and a maximum rate;
   user-operable means connected to the device; and
   means for determining whether a user has operated said user-operable means in accordance with at least one predetermined criterion, said determining means being connected to said establishing means and operating in a manner that when a user has failed to operate said user-operable means in accordance with said at least one criterion, said medication administration rate is set at said emergency rate.

2. The device of claim 1, further comprising means for measuring a total quantity of medication which has been administered after a user has most recently operated said user-operable means, said measuring means being connected to said determining means, and wherein said at least one criterion includes operation of said user-operable means before said total quantity exceeds a qualifying dose.

3. The device of claim 2, wherein said determining means is operable to vary said qualifying dose.

4. The device of claim 1, further comprising means for measuring a total time which has elapsed after a user has most recently operated said user-operable means, said measuring means being connected to said determining means, and wherein said at least one criterion includes operation of said user-operable means before said total time exceeds a qualifying time.

5. The device of claim 4, wherein said determining means is operable to vary said qualifying time.

6. The device of claim 4, wherein said qualifying time is varied as a function of the time of day.

7. The device of claim 6, wherein said determining means operates in a manner that when a user operates said user-operable means before said total time has exceeded said qualifying time, said at least one criterion is updated as a function of the time of day and said measuring means is reset to begin measuring total time once again.

8. The device of claim 7, further comprising means for delivering a reminder indication to a user prior to when said total time has exceeded said qualifying time, said delivering means being connected to said determining means.

9. The device of claim 8, wherein said delivering means operates to deliver said reminder indication when said measuring means is reset.

10. The device of claim 1, wherein said user-operable means is operatively connected to said establishing means, whereby said medication administration rate may be varied at mealtimes.

11. The device of claim 1, further comprising an alarm connected to said determining means, and wherein said determining means operates in a manner that when a user has failed to operate said user-operable means in accordance with said at least one criterion, said alarm is activated.

* * * * *